United States Patent [19]

Jackson et al.

[11] Patent Number: 4,537,075
[45] Date of Patent: Aug. 27, 1985

[54] POSITION CONTROL

[75] Inventors: Graham Jackson, Lancashire; Ryszard Surawy, Chippenham, both of England

[73] Assignee: British Aerospace Public Limited Company, London, England

[21] Appl. No.: 616,780

[22] Filed: Jun. 1, 1984

Related U.S. Application Data

[63] Continuation of Ser. No. 401,218, Jul. 23, 1982, abandoned.

[30] Foreign Application Priority Data

Jul. 25, 1981 [GB] United Kingdom ......... 8123024

[51] Int. Cl.³ .............................................. G01N 29/00
[52] U.S. Cl. ................................................... 73/634
[58] Field of Search ........................... 73/634, 625, 628

[56] References Cited

U.S. PATENT DOCUMENTS 2,743,429 4/1956 Erdman et al. .................... 73/634
2,751,783 6/1956 Erdman ............................. 73/634
3,898,838 8/1975 Connelly ........................... 73/634
3,969,926 7/1976 Walker et al. ..................... 73/634
3,978,714 9/1976 Schraiber et al. ................. 73/634

Primary Examiner—Stephen A. Kreitman
Attorney, Agent, or Firm—Cushman, Darby & Cushman

[57] ABSTRACT

In ultrasonic echo testing to detect flaws in manufactured articles, raw materials and such it is desirable to maintain a predetermined spacing and relative orientation of the ultrasonic transducer and the surface of the tested article. Thus, automatic scanning of the article by repetitively translating the transducer across its surface is difficult or impossible if the article surface is anything other than flat. Herein, a plurality of satellite transducers are mounted with and around a primary transducer on a motor-adjustable articulated transducer head in ultrasonic test equipment so as to receive part of the main beam echo and thereby produce respective distance signals, which signals are used by control apparatus to control the transducer head adjustment motor and thereby regulate the primary transducer position relative to the tested article.

9 Claims, 4 Drawing Figures

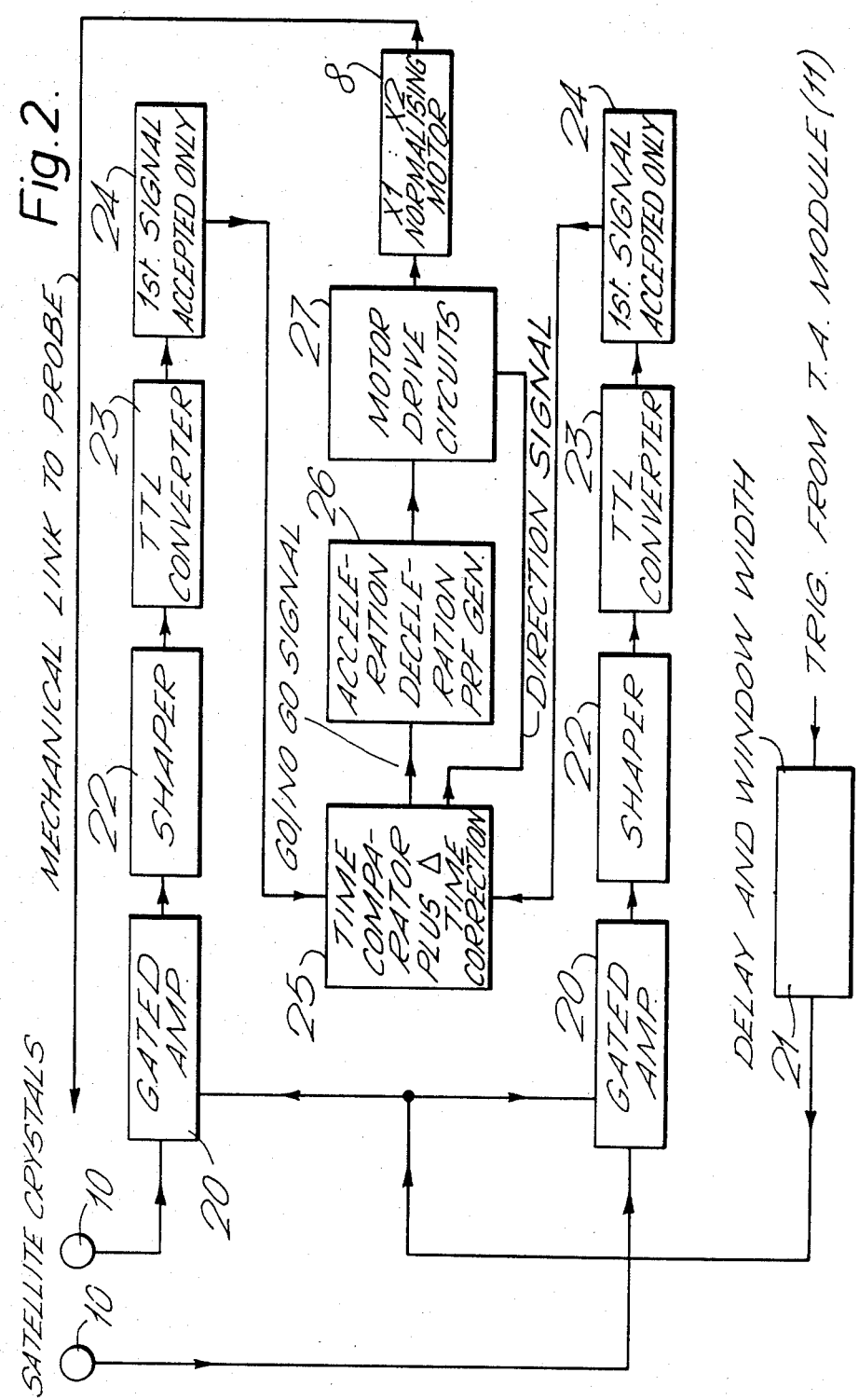

POSITION CONTROL

This is a continuation of application Ser. No. 401,218, filed July 23, 1982, now abandoned.

This invention relates to a method and apparatus for controlling the position of a first member relative to a second member. More particularly, but not exclusively, it relates to the position control of an ultrasonic transducer probe, used in test apparatus for detecting flaws in articles such as semi-finished products, raw materials and manufactured components, such that a beam of ultrasonic waves emitted by the transducer remains at a constant angle of incidence on the surface of a tested article.

A known item of ultrasonic testing apparatus comprises a water tank for receiving the article to be tested, a translation mechanism above the tank, and a probe which is supported by the translation mechanism and extends down into the water to just above the article. An ultrasonic transducer head is connected to the lower end of the probe and coupled by a linkage to an adjustment mechanism, a servomotor or manual mechanism for example, whereby the orientation of the head and the distance between the transducer and the article can be adjusted so that a pulsed beam of ultrasonic energy emitted from the head is incident normal to the surface of the article. Said adjustments, once made, are not normally capable of alteration whilst the system is in motion during the scanning of the article. An image corresponding to an echo received from the article is displayed on say an oscilloscope and the translation mechanism is operable for moving the probe so that the transducer head scans across the article. In further known apparatus the article to be tested is not immersed in water—instead, this is emitted as a jet from a nozzle incorporated into the transducer head, the jet impinging on the article and defining a path for the ultrasonic energy.

Since the ultrasonic beam must remain at least substantially normal to the surface of the article to be tested, or at least should remain at a constant angle of incidence on that surface, and at a substantially constant distance from said surface, the usefulness of the known equipment is limited, for example it cannot be used in an automatic scanning mode to test articles having a curved or profiled surface.

According to one aspect of the invention, there is provided apparatus for controlling the position of a first member relative to a second, the apparatus comprising two transducers supported by said first member and operable for producing signals indicative of respective distances from the transducers to a position on the second member, drive motor means coupled to the first member for moving the first member relative to the second, and control means for receiving said signals and for controlling said drive motor means.

According to a second aspect of the present invention there is provided apparatus for controlling the position of a first member relative to a second, the apparatus comprising a primary transducer with two or more secondary transducers supported by said first member and operable for producing signals indicative of respective distances from the transducers to a position on the second member, drive motor means coupled to the first member for moving the first member relative to the second, and control means for receiving said signals and for controlling said drive motor means, the said controlled movements of the first member, relating the distance and angular position of the transducer to the workpiece, being continuously and automatically adjusted during the scanning of the workpiece.

For a better understanding of the invention, reference will now be made, by way of example, to the accompanying drawings, in which:

FIG. 2 is a simplified diagram of a control unit used with the apparatus of FIG. 1, and FIGS. 3 and 4 are diagrammatic, sectional views of transducer heads for use in ultrasonic testing apparatus.

Figure 1:
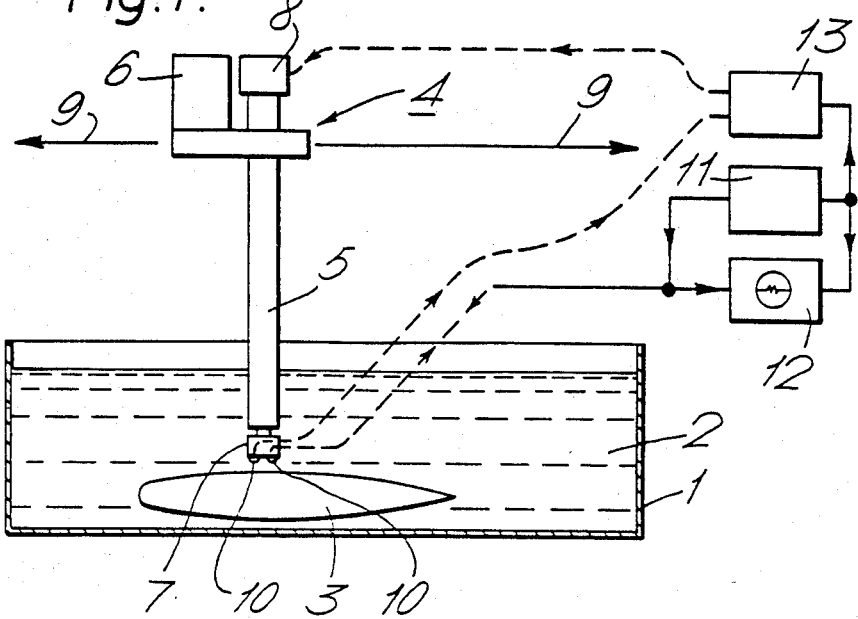
FIG. 1 is a diagrammatic view of immersion-type ultrasonic testing apparatus.

The FIG. 1 apparatus comprises a tank 1 containing water 2 and, in the water, an article 3 to be tested, the surface of the article being curved in the plane of the drawing. Above the tank is a probe assembly 4 comprising a hollow probe column 5 which extends down to above article 3 and an adjustment mechanism 6 for adjusting the depth of entry of the probe into the water, for turning it about its axis and so on. A transducer head 7 is hinged to the lower end of the probe so that it can pivot about an axis perpendicular to the drawing and the adjustment mechanism 6 includes a servomotor 8 coupled to the transducer head 7 via a linkage (not shown), for example a chain drive extending inside the probe, for controlling the pivoting movement of the transducer head. The probe assembly is supported by means (not shown) such that it can be moved in the directions of arrows 9 and perpendicular thereto to scan over the surface of article 3. By way of example (not shown), the probe assembly might be carried on a wheeled troller running on cross-rails which themselves are wheeled and able to move along longitudinal rails, suitable drive motors being coupled to the wheels to produce the movement. The transducer head 7 incorporates a main transducer crystal (not shown) for directing a pulsed beam of ultrasonic energy down onto the surface of the article 3 and for receiving echoes from the article. The head also comprises two auxiliary or satellite transducer crystals 10 positioned on the lower face of the head 7 at respective sides of the position from which the ultrasonic beam is emitted.

The main transducer crystal is connected to a supply unit 11 which produces a series of sharp pulses for driving the crystal in known manner and signals representative of echoes received by the crystal are displayed on a c.r.t. monitor 12. The satellite transducer crystals 10 also receive the echoes, the times at which they are received by the respective crystals 10 being dependent upon the angle of incidence between the beam and the surface of article 3 from which the echoes are reflected. Accordingly, the crystals 10 are connected to a control unit 13 which determines the relative timing of the echoes received by these crystals and correspondingly controls the servomotor 8 to make the ultrasonic beam normal to the surface.

If the transducer head 7 is made so that the crystals 10 are exactly equidistant from the beam and in a plane to which the beam is exactly normal, the echoes received by the respective crystals 10 will coincide, in time, when the beam is normal to the surface of article 3. If the transducer head is not as described, either by design choice or due to manufacturing tolerance, then there will be a constant time differential to take into account. The control unit 13 shown in FIG. 2 is adapted to do this. Also, as will be appreciated, the transducer crystals receive echoes not only from the top surface of article 3 but also from its bottom surface and, in fact, may receive a series of spurious echoes as well. The FIG. 2 control unit includes means for defining time windows, synchronised to the operation of supply unit 11, to ensure that only the relevant echoes are acted upon. These will normally be the echoes reflected from the upper surface of the article 3 but in some cases it may be desirable to use the echoes from say the lower surface or even some internal surface. The ultrasonic beam is controlled to be normal to whichever surface reflects the chosen echoes. The time window defining means could be made adjustable so as to enable an operator to select the surface as desired.

Referring now to FIG. 2, the signals from the two satellite transducers 10 are fed to respective gated amplifiers 20 which are controlled by the aforementioned window defining means, this taking the form of a pulse generator 21 which, in response to each pulse from supply unit 11, produces after a predetermined or controllable variable delay a pulse of predetermined width for "opening" the amplifiers 20. The echo signals passed by the amplifiers while "open" are shaped by respective shaping circuits 22 and converter circuits 23, these converter circuits also adapting the signal levels to suit the "transistor-transistor logic" (TTL) circuitry which, because of its suitability from the point of view of speed of operation, is preferably used for the remaining parts of the control unit. The pulse outputs from circuits 23 are passed to respective circuits 24 which each pass only the first pulse received thereby, any further such pulses generally corresponding to spurious echoes, and these first pulses are passed to a logic circuit 25 which compares the time between them with a predetermined or controllably variable error time appropriate to the aforementioned differential due to manufacturing inaccuracies in the head 7 for example. In dependence upon the comparison, circuit 25 decides whether or not a correction of the position of transducer head 7 is necessary and, accordingly, passes a "Go" or "No Go" signal to a pulse generating circuit 26. The circuit 26, in response to a "Go" signal, produces a pulse train of which the repetition frequency first rises smoothly to a predetermined level, then remains constant for a time and then decreases smoothly, the object being to drive motor 8, via motor drive circuit 27, through a predetermined adjustment step while taking into account the acceleration and deceleration capabilities of the motor. Meanwhile, the logic circuit 25 also produces a direction indicating signal, dependent on which of the two crystals 10 was the first to receive an echo, for ensuring that drive circuit 27 drives motor 8 in the appropriate direction. The construction of drive circuit 27 depends on the form of motor 8. For example, if motor 8 is a stepping motor, circuit 27 could comprise a suitable logic circuit for passing on the pulses from generator 26 in appropriate sequence to step the motor in the correct direction. For a d.c. motor, the drive circuit might comprise a frequency/voltage converter for example.

It will be appreciated that transducer head 7 could be so coupled to probe column 5 that it can pivot about two perpendicular axes and thereby be adjustable to allow for curvature of the surface of article 3 in more than one direction, an additional servomotor being provided to control the pivoting about the additional axis. Then the transducer head can be provided with two more satellite transducers so that there are four of these at 90° intervals around the ultrasonic beam and the circuit of FIG. 2 can be duplicated to control the additional servomotor in response to signals from the additional two satellite transducers.

Figure 3:
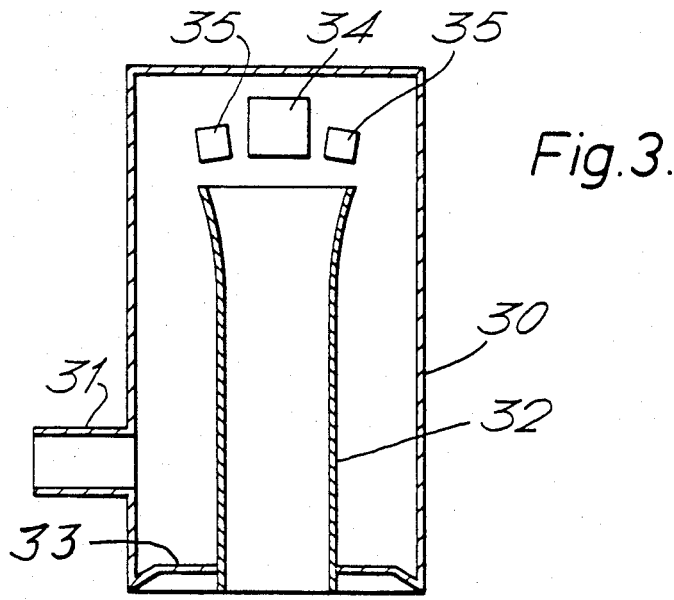

It will be appreciated that the invention can be applied to testing apparatus using jet probes instead of the immersion type apparatus of FIG. 1. FIG. 3 shows a transducer head for a jet probe in the form of a hollow enclosure 30 with an entry 31 for pressurised water and an outlet tube 32 extending from the lower wall 33 of the enclosure to near a main transducer crystal 34 within the enclosure. Water supplied through entry 31 fills the enclosure 30 and flows as a jet from tube 32. Two or four satellite crystals 35 (only two are shown) are positioned at respective sides of the crystal 34. The tube 32 is slightly belled-out over its top third or so to act as a kind of waveguide which allows the returned ultrasonic echoes to reach the satellite crystals 35, and thereby enable automatic control of the head position in the same way as described with reference to FIGS. 1 and 2. Crystals 35 are slightly inclined to face more exactly the direction of arrival of the echo signals (such inclination is not of course essential but may improve sensitivity).

Figure 4:
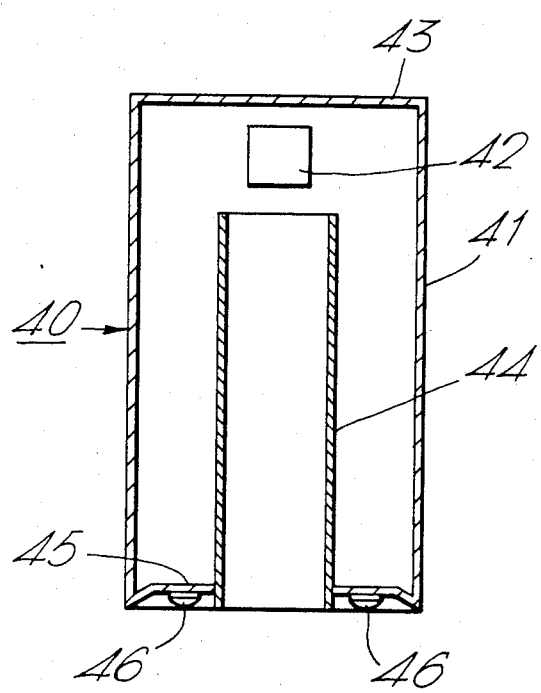

FIG. 4 shows a transducer head 40 comprising an enclosure 41 with a main transducer crystal 42 inside the enclosure near one end wall 43 thereof. A signal guide tube 44 extends within the enclosure from rear crystal 42 to an exit at the other end wall 45 of the enclosure, this wall being dished to act as an ultrasonic reflector plate. Two or four satellite transducer crystals 46 (only two are shown) are attached to the outer surface of wall 45 around the exit of tube 42. Suitable pivot mounting means (not shown) is provided affixed to the wall 43 for attaching the transducer head to a probe, for example the probe of FIG. 1.

Instead of the satellite transducers 10 and 46 being attached to the lower face of the transducer head, they could be mounted elsewhere, for example on suitable support arms extending laterally from the head. Also, it is not essential that they be used at all. Instead the relative orientation of the head and article to be tested could be sensed using say two transducers which sense their respective distances from the surface of the article by measuring variations of capacitance or inductance induced therein by the article or there could even be a mechanical probe arrangement which contacts the surface of the article to sense its position.

Where the ultrasonic transducers are provided, the echoes from an ultrasonic signal other than that emitted by the main transducer in head 7 may be detected, for example each satellite transducer may be driven to produce its own beam, perhaps at a frequency different from that of the main transducer, and the control unit adapted to act on signals representing echoes of the beams produced by the satellite transducers.

Finally, although embodiments of the invention applied to ultrasonic testing apparatus have been described, the invention may also be applicable to other situations where one member is to have its position controlled in relation to another, for example in relation to some automatic machine tools and other kinds of test apparatus.

The satellite transducers 10 in FIG. 1 or 46 in FIG. 4 could be mounted so that their respective reception field axes are parallel to the beam axis of the primary transducer or it may improve the sensitivity of the apparatus if each satellite transducer is mounted so that its reception field axis is inclined inwardly towards or outwardly away from the primary transducer beam axis.

We claim:

1. Ultrasonic test equipment, comprising a transducer head having primary transducer means, mounted on said transducer head, for emitting a pulsed beam of ultrasonic energy towards a workpiece to be tested and for receiving energy reflected back from said workpiece for subsequent formation of signals indicative of workpiece flaws;

drive pulse supply means, connected to said primary transducer means, for causing said primary transducer means to emit said beam; and motor drive support system means for relatively moving said workpiece and transducer head to scan said beam across said workpiece and, during such scanning, for automatically regulating the angle of incidence between said beam and a surface of said workpiece, said support system means including at least two receive-only satellite transducers supported by said transducer head at respective sides of the axis of said beam so as to receive respective portions of said reflected energy of each pulse of said beam emitted by said primary transducer means at respective times dependent upon said angle of incidence, an angle control motor and associated motor drive circuit means for relatively moving said transducer head and workpiece to vary said angle of incidence, and time comparator means, connected between said satellite transducers and said motor drive circuit means for controlling said drive circuit means by comparing the timing of said respective reflected energy pulses received by said satellite transducers.

2. Equipment according to claim 1, wherein said transducer head comprises a hollow housing having said primary transducer means and said satellite transducers mounted therein, said satellite transducers being positioned at respective sides of said primary transducer means, and said housing defining an opening in said housing for exit of said emitted beam and entry of said reflected energy.

3. Equipment according to claim 2 further comprising a tubular duct fixed adjacent said opening and extending inside said housing to a position near said transducers, at which position said duct has a bell mouth which widens out towards said satellite transducers; and an inlet in said housing for receiving a pressurised supply of water wherein said duct directs a jet of said water towards said workpiece.

4. Equipment according to claim 1, wherein said support system means further comprises discriminating means, operatively connected to said time comparator means and to said drive pulse supply means, for defining a predetermined time window following each emitted beam pulse, said time windows enabling said time comparator means to be responsive to said reflected energy pulses received by said satellite transducers.

5. Equipment according to claim 4, wherein said discriminating means comprises respective controllable gate devices connected between said satellite transducers and said time comparator means, window pulse generating means connected to said drive pulse supply means and a control input of each gate device and operable to generate a gate device opening pulse of predetermined length starting after a predetermined delay from the reception of a pulse from the drive pulse supply means.

6. Equipment according to claim 1, wherein said time comparator means comprises respective signal shaping means, connected to receive said reflected energy received by said satellite transducers, for producing a shaped output pulse in response to a first satellite transducer pulse received by said shaping means after each emitted beam pulse, logic circuit means, connected to said signal shaping means, for forming a first output signal having one of two values indicative of whether said shaped output pulses from said signal shaping means are coincident in time, and for forming a second output signal having a value indicative of which of said shaped output pulses is the first to arrive at said logic circuit means, and pulse train generating means, connected between said logic circuit means and said motor drive circuit means, and forming, in response to said first output signal taking the value which indicates that said shaped output pulses are not coincident in time, a pulse train incorporating an initial acceleration phase in which repetition frequency of pulses of said pulse train increases up to a predetermined value and incorporating an end deceleration phase in which said repetition frequency decreases from said predetermined value, said motor drive circuit means being connected to receive said pulse train from said pulse train generating means and said second output signal from said logic circuit means, and said motor drive circuit means subsequently driving said angle control motor at a speed dependent upon the pulse repetition rate of said pulse train and in a direction dependent upon said output signal.

7. Ultrasonic test equipment, comprising transducer head means for directing a pulsed beam of ultrasonic energy towards a workpiece and for receiving energy reflected back from said workpiece; and motor drive support system means for relatively moving said workpiece and said transducer head and, during such movement, for automatically controlling the relative position of said transducer head and workpiece so as to regulate the angle of incidence between said beam and a surface of said workpiece surface; wherein said transducer head means comprises a housing, a primary transducer within said housing for producing pulses of ultrasonic energy and for receiving said reflected energy, at least two receive-only satellite transducers mounted within said housing at respective sides of said primary transducer so as to receive respective portions of said reflected energy and output respective electrical signals indicative thereof, and duct means extending between an aperture in a wall of said housing and a position adjacent said transducers, at which position the duct means defines a bell mouth opening towards said transducers, wherein said duct means directs energy produced by said primary transducer to form a directional energy beam emitted from said aperture and also directs said reflected energy back to said transducers, and wherein said support system means includes means for deriving a signal for controlling the relative position of said transducer head and workpiece by comparing the timing of said respective electrical output signals produced by said satellite transducers.

8. Equipment according to claim 7, wherein said transducer head housing has an entry for receiving a pressurised supply of water and said duct means further functions as a squirter nozzle for producing a jet of said water.

9. Equipment according to claim 7, wherein said support system means further comprises support means for supporting said workpiece for testing thereof and probe means, movably supported by a carrier assembly, for selectively moving said probe means towards and away from said workpiece, said carrier assembly being supported for movement with respect to said support means for translation of said probe means past a surface of said workpiece, and said transducer head means is pivotably attached to said probe means, said support system means also further comprising drive motor means coupled to said probe means for controlling said movement of said carrier assembly towards and away from said workpiece and for pivotably moving said transducer head means relative to said probe means, and comprising control means, connected to said satellite transducers and said drive motor means, for responding to said satellite output signals to maintain a predetermined distance between said workpiece surface and said primary transducer and to maintain a predetermined angle of incidence between the axis of said ultrasonic energy beam and said workpiece surface.

* * * * *